United States Patent
Wang et al.

(10) Patent No.: US 12,344,769 B2
(45) Date of Patent: Jul. 1, 2025

(54) METHOD FOR EXTRACTING GELATIN

(71) Applicant: Novozymes A/S, Bagsvaerd (DK)

(72) Inventors: Mingzhu Wang, Beijing (CN); Yu Zhang, Beijing (CN); Yazhen Wang, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 884 days.

(21) Appl. No.: 17/439,859

(22) PCT Filed: Apr. 7, 2020

(86) PCT No.: PCT/CN2020/083470
§ 371 (c)(1),
(2) Date: Sep. 16, 2021

(87) PCT Pub. No.: WO2020/207370
PCT Pub. Date: Oct. 15, 2020

(65) Prior Publication Data
US 2022/0186079 A1    Jun. 16, 2022

(51) Int. Cl.
*C12P 19/00* (2006.01)
*C09H 3/00* (2006.01)
*C09H 7/00* (2006.01)
*C12P 21/06* (2006.01)

(52) U.S. Cl.
CPC ............... *C09H 3/00* (2013.01); *C09H 7/00* (2013.01); *C12P 21/06* (2013.01)

(58) Field of Classification Search
CPC ......... C12P 21/06; C12Y 304/21; C09H 3/00; C09H 7/00

USPC ....................................................... 435/69.1
See application file for complete search history.

(56) References Cited

U.S. PATENT DOCUMENTS

| 4,220,724 | A | 9/1980 | Berg |
| 10,138,473 | B2 | 11/2018 | Matsui |
| 2002/0165359 | A1 | 11/2002 | Lafargue |
| 2012/0309067 | A1 | 12/2012 | Matsui |

FOREIGN PATENT DOCUMENTS

| CA | 2447566 A | 4/2005 |
| CN | 102051130 A | 11/2010 |
| CN | 101921821 A | 12/2010 |
| CN | 102329843 A | 1/2012 |
| EP | 0999248 A1 | 5/2000 |
| JP | 2003034699 A | 2/2003 |
| WO | 2019/046232 A1 | 3/2019 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Ahmad et al_2017_Food Hydrocolloids 63_85-96.

* cited by examiner

*Primary Examiner* — Tekchand Saidha
*Assistant Examiner* — Mohammad Y Meah
(74) *Attorney, Agent, or Firm* — Yoshimi D. Barron

(57) ABSTRACT

Provided is an enzymatic method of extracting high quality gelatin from collagen containing material.

9 Claims, No Drawings

Specification includes a Sequence Listing.

SEQUENCE LISTING

<160> NUMBER OF SEQ ID NOS: 1

<210> SEQ ID NO 1
<211> LENGTH: 355
<212> TYPE: PRT
<213> ORGANISM: Thermoascus aurantiacus
<220> FEATURE:
<221> NAME/KEY: SIGNAL
<222> LOCATION: (1)..(19)
<220> FEATURE:
<221> NAME/KEY: PROPEP
<222> LOCATION: (20)..(178)
<220> FEATURE:
<221> NAME/KEY: mat_peptide
<222> LOCATION: (179)..()

<400> SEQUENCE: 1

```
Met Arg Leu Val Ala Ser Leu Thr Ala Leu Val Ala Leu Ser Val
            -175                -170                -165

Pro Val Phe Pro Ala Ala Val Asn Val Lys Arg Ala Ser Ser Tyr
            -160                -155                -150

Leu Glu Ile Thr Leu Ser Gln Val Ser Asn Thr Leu Ile Lys Ala
            -145                -140                -135

Val Val Gln Asn Thr Gly Ser Asp Glu Leu Ser Phe Val His Leu
            -130                -125                -120

Asn Phe Phe Lys Asp Pro Ala Pro Val Lys Lys Val Ser Val Tyr
            -115                -110                -105

Arg Asp Gly Ser Glu Val Gln Phe Glu Gly Ile Leu Ser Arg Tyr Lys
            -100                -95                 -90

Ser Thr Gly Leu Ser Arg Asp Ala Phe Thr Tyr Leu Ala Pro Gly Glu
            -85                 -80                 -75

Ser Val Glu Asp Val Phe Asp Ile Ala Ser Thr Tyr Asp Leu Thr Ser
    -70                 -65                 -60

Gly Gly Pro Val Thr Ile Arg Thr Glu Gly Val Val Pro Tyr Ala Thr
-55                 -50                 -45                 -40

Ala Asn Ser Thr Asp Ile Ala Gly Tyr Ile Ser Tyr Ser Ser Asn Val
                -35                 -30                 -25

Leu Thr Ile Asp Val Asp Gly Ala Ala Ala Thr Val Ser Lys Ala
                -20                 -15                 -10

Ile Thr Pro Leu Asp Arg Arg Thr Arg Ile Ser Ser Cys Ser Gly Ser
        -5                  -1  1                   5

Arg Gln Ser Ala Leu Thr Thr Ala Leu Arg Asn Ala Ala Ser Leu Ala
10                  15                  20                  25

Asn Ala Ala Ala Asp Ala Ala Gln Ser Gly Ser Ala Ser Lys Phe Ser
                30                  35                  40

Glu Tyr Phe Lys Thr Thr Ser Ser Ser Thr Arg Gln Thr Val Ala Ala
                45                  50                  55
```

```
Arg Leu Arg Ala Val Ala Arg Glu Ala Ser Ser Ser Ser Gly Ala
        60              65                  70

Thr Thr Tyr Tyr Cys Asp Asp Pro Tyr Gly Tyr Cys Ser Ser Asn Val
    75              80                  85

Leu Ala Tyr Thr Leu Pro Ser Tyr Asn Ile Ile Ala Asn Cys Asp Ile
90              95                  100                     105

Phe Tyr Thr Tyr Leu Pro Ala Leu Thr Ser Thr Cys His Ala Gln Asp
            110                 115                 120

Gln Ala Thr Thr Ala Leu His Glu Phe Thr His Ala Pro Gly Val Tyr
            125                 130                 135

Ser Pro Gly Thr Asp Asp Leu Ala Tyr Gly Tyr Gln Ala Ala Met Gly
        140                 145                 150

Leu Ser Ser Ser Gln Ala Val Met Asn Ala Asp Thr Tyr Ala Leu Tyr
    155                 160                 165

Ala Asn Ala Ile Tyr Leu Gly Cys
170             175
```

METHOD FOR EXTRACTING GELATIN

CROSS-REFERENCE TO RELATED APPLICATIONS

This application is a 35 U.S.C. 371 national application of international application no. PCT/EP2020/083470 filed Apr. 7, 2020, which claims priority or the benefit under 35 U.S.C. 119 of international application no. PCT/CN2019/081704 filed Apr. 8, 2019. The content of each application is fully incorporated herein by reference.

TECHNICAL FIELD

The present invention relates to an enzymatic method of extracting high quality gelatin from collagen containing material.

REFERENCE TO A SEQUENCE LISTING

This application contains a Sequence Listing in computer readable form. The computer readable form is incorporated herein by reference.

BACKGROUND OF THE INVENTION

Gelatin is a mixture of peptides and proteins obtained by solubilizing collagen. Collagen is predominantly extracted from various animal by-products such as bones and skin using an alkaline or acid pretreatment.

Enzymatic processes for extracting gelatin from collagen have been described. The enzymes are generally used to either improve or replace a pretreatment step in the gelatin process, such as liming, or to increase the yield gelatin during hot water extraction at a lower temperature.

CN102051130 compares the use of an acid protease, pepsin, and several neutral proteases for the extraction of gelatin from defatted demineralized bones. CN102329843 discloses the use of an acid protease from *A. niger* for the extraction of gelatin from bone collagen.

High quality gelatin yield is relatively low within the disclosed enzymatic extraction process, which impact the average bloom of the gelatin obtained. Therefore, there is still a desire to provide an improved process for enzymatically extracting gelatin wherein a high quality of the gelatin is obtained at a high yield.

SUMMARY OF THE INVENTION

The present invention relates to a process for extracting gelatin, comprising (a) incubating a collagen containing material in the presence of an effective amount of a protease, and (b) preparing extracting the gelatin from the collagen containing material, wherein the protease is a metalloprotease belonging to family M35.

In a preferred embodiment, wherein the protease is selected from the group consisting of:
(i) a polypeptide comprising or consisting of an amino acid sequence having at least 85%, preferably at least 90%, more preferably at least 91%, more preferably at least 92%, even more preferably at least 93%, most preferably at least 94%, and even most preferably at least 95%, such as even at least 96%, 97%, 98%, 99% or 100% identity to amino acids 1-177 of the amino acid sequence SEQ ID NO: 1;
(ii) a polypeptide comprising a substitution, deletion, and/or insertion of one or more (e.g., several) amino acids of amino acids 1-177 of the amino acid sequence of SEQ ID NO: 1.

Surprisingly it was found that incubating the material comprising collagen with an acid protease as disclosed herein, the yield of high quality gelatin obtained, the total yield and/or the average bloom strength of the total gelatin obtained was higher than that of the gelatin obtained with enzymatic processes known in the art, which also can ensure a high average bloom strength of the total gelatin product.

In a preferred embodiment, the process comprises the following steps: providing a collagen containing material, demineralizing the collagen containing material to produce ossein, and contacting the said protease to the ossein.

In a preferred embodiment, the protease is derived from genus *Thermoascus*, preferably from *Thermoascus aurantiacus*, and most preferably from *Thermoascus aurantiacus* CGMCC No. 0670.

In a preferred embodiment, the process comprises a step of raising the temperature to deactivate the protease after incubation, preferably, the total time for heating and temperature keeping is at least 10 minutes, after the deactivation step an amount of gelatin is extracted and collected.

In a preferred embodiment, the process comprises a step of raising the temperature after incubation to where the protease is deactivated by keeping for, preferably, at least 5 mins, after which an amount of gelatin is extracted and collected.

In a preferred embodiment, the process comprises a step of a multi-grade extraction, preferably, comprising the step of extraction of the gelatin during a step-by-step heating process, preferably, the temperature of the extraction is performed at a temperature of between 50° C. and 100° C.

In a preferred embodiment, wherein an acid is added to the collagen containing material for demineralizing.

In a preferred embodiment, wherein the ossein is grinded to particles that can pass 10 meshes preferably 20 meshes sieves before incubation.

In a preferred embodiment, wherein the incubation is performed at a temperature of between 20° C. to 40° C., and/or at a pH of between 4 and 6.

The present invention also relates to a gelatin obtainable by a method mentioned above.

DETAILED DISCLOSURE OF THE INVENTION

The present invention relates to a process for preparing gelatin comprising (a) incubating a collagen containing material in the presence of an effective amount of a protease, and (b) extracting the gelatin from the collagen containing material, wherein the protease is a metalloprotease belonging to family M35.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at http://www.chem.qmw.ac.uk/iubmb/enzyme/index.html). Proteases are also called, e.g., peptidases, proteinases, peptide hydrolases, or proteolytic enzymes.

The proteases for use according to the invention are of the endo-type that act internally in polypeptide chains (endopeptidases). There are no limitations on the origin of the protease for use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared, which is generally known in the art, e.g., by site-directed mutagenesis, by PCR (using a PCR fragment containing the desired mutation as one of the primers in the PCR reactions), or by random mutagenesis. The preparation of consensus proteins is described in e.g. EP 897985. Examples of protease variants, as used in the present context, are proteases in which one or more amino acids have been deleted, inserted or substituted with other amino acids.

Proteases are classified on the basis of their catalytic mechanism into the following groups: Serine proteases (S), Cysteine proteases (C), Aspartic proteases (A), Metalloproteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In some preferred embodiments, the metalloproteases belonging to family M35 was defined at pp. 1492-1495 of the above Handbook.

In some preferred embodiments, metalloproteases are hydrolases in which the nucleophilic attack on a peptide bond is mediated by a water molecule, the water molecule being activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

For determining whether a given protease is a metalloprotease or not, reference is made to the above Handbook and the principles indicated therein. Such determination can be carried out for all types of proteases, be it naturally occurring or wild-type proteases; or genetically engineered or synthetic proteases.

The present invention relates to a process for preparing gelatin comprising (a) incubating a collagen containing material with a protease, and (b) extracting the gelatin from the collagen containing material, wherein the protease is a metalloprotease belonging to family M35.

In some preferred embodiments, wherein the protease is selected from the group consisting of:
(i) a polypeptide comprising or consisting of an amino acid sequence having at least 85%, preferably at least 90%, more preferably at least 91%, more preferably at least 92%, even more preferably at least 93%, most preferably at least 94%, and even most preferably at least 95%, such as even at least 96%, 97%, 98%, 99% or 100% identity to amino acids 1-177 of the amino acid sequence SEQ ID NO: 1;
(ii) a polypeptide comprising a substitution, deletion, and/or insertion of one or more (e.g., several) amino acids of amino acids 1-177 of the amino acid sequence of SEQ ID NO: 1.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

An exact match occurs when the two sequences have identical amino acid residues in the same positions of the overlap. The length of a sequence is the number of amino acid residues in the sequence (e.g., the length of amino acids 1-177 of SEQ ID NO: 1 herein is 177).

The term "variant" means a polypeptide having protease activity comprising an alteration, i.e., a substitution, insertion, and/or deletion at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. When variants are described, the nomenclature described below is adapted for ease of reference. The accepted IUPAC single letter or three letter amino acid abbreviation is employed.

In a preferred embodiment, the homologous polypeptides have an amino acid sequence that differs by forty, thirty-five, thirty, twenty-five, twenty, or fifteen amino acids. In another embodiment, the homologous polypeptides have an amino acid sequence that differs by ten, nine, eight, seven, six, or five amino acids. In another particular embodiment, the homologous polypeptides differ by four, three, two amino acids, or one amino acid from amino acids 1-177 of SEQ ID NO: 1 herein.

An allelic variant denotes any of two or more alternative forms of a gene occupying the same chromosomal locus. Allelic variation arises naturally through mutation and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from amino acids 1-177 of SEQ ID NO: 1 herein by an insertion or deletion of one or more amino acid residues and/or a substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverses.

In one embodiment, the protease for use according to the invention is a fungal protease, the term fungal indicating that the protease is derived from, or originates from, a fungal, or is an analogue, a fragment, a variant, a mutant, or a synthetic protease derived from a fungal. It may be produced or expressed in the original wild-type fungal strain, in another microbial strain, or in a plant; i.e., the term covers the expression of wild-type, naturally occurring proteases, as well as expression in any host of recombinant, genetically engineered or synthetic proteases.

In one embodiment, the protease for use according to the invention may be derived from microorganisms of any genus. For purposes of the present invention, the term "derived from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one embodiment, the protease is derived from a yeast such as a *Candida, Kluyveromyces, Pichia, Saccharomyces, Schizosaccharomyces*, or *Yarrowia* polypeptide; or more preferably a fungi such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma*. In another embodiment the protease is derived from *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Thermoascus aurantiacus, Trichoderma harzianum, Trichoderma koningii, Trichoderma longibrachiatum, Trichoderma reesei*, or *Trichoderma viride*.

In a preferred embodiment, the protease is derived from a fungus of the genus *Thermoascus*, for example the species *Thermoascus aurantiacus*, such as the strain *Thermoascus aurantiacus* CGMCC No. 0670.

In a preferred embodiment, the protease derived from *Thermoascus aurantiacus* comprises or consists of amino acids 1-177 of SEQ ID NO: 1 herein.

In a preferred embodiment, the protease of the invention is a variant of the protease of amino acids 1 to 177 of SEQ ID NO: 1. It is not identical to amino acids 1 to 177 of SEQ ID NO: 1, as it comprises at least one modification as compared to amino acids 1 to 177 of SEQ ID NO: 1.

In a preferred embodiment, the variant of the protease of amino acids 1 to 177 of SEQ ID NO: 1 herein, which consists of the following modification: A27K/D79L/Y82F/S87G/D104P/A112P/A126V/D142L, is another example of a second protease of the invention. The position numbers refer to the position numbering of amino acids 1 to 177 of SEQ ID NO: 1.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In the process of the invention the protease may be purified. The term "purified" as used herein covers enzyme protein essentially free from components from the organism from which it is derived. The term "purified" also covers enzyme protein free from components from the native organism from which it is obtained, this is also termed "essentially pure" enzyme and may be particularly relevant for enzymes which are naturally occurring and which have not been modified genetically, such as by deletion, substitution or insertion of one or more amino acid residues.

Accordingly, a protease may be purified, viz. only minor amounts of other proteins being present. The expression "other proteins" relates in particular to other enzymes. The term "purified" as used herein also refers to removal of other components, particularly other proteins and most particularly other enzymes present in the cell of origin of the protease. A protease may be "substantially pure", i.e., substantially free from other components from the organism in which it is produced, e.g., a host organism for recombinantly produced enzyme. Preferably, the protease is at least 75% (w/w) pure, more preferably at least 80%, 85%, 90% or even at least 95% pure. In a still more preferred embodiment, the protease is an at least 98% pure enzyme protein preparation.

However, for the uses according to the invention, the protease need not be that pure. It may e.g. include other enzymes, even other proteases, in which case it could be termed a protease preparation.

In some preferred embodiments, the process of the present invention comprises the following steps: providing a collagen containing material; demineralizing the collagen containing material to produce ossein; and adding the said protease to the ossein.

Typical collagen containing materials include skins, bones, hides and connective tissue of an animal body. Sources of animal bodies include cow, pig, fish and sheep. The most preferred source for collagen for production of high quality gelatin is cow bone.

In some preferred embodiments, the bone raw materials are first crushed to grains with size between 8~50 mm, then the bone is degreased by boiling at 80~95° C. for 2-8 hs for degreasing. The grease can be collected for relevant application as food flavours while the degreased bone will go the demineralization process for gelatin producing. The degreased bone can be produced onsite or purchased from market.

In some preferred embodiments, wherein an acid is added to the collagen containing material for demineralizing. Usually, the degreased bone is demineralized to get a material, ossein, with rich contents of collagen. For example, the degreased bone is soaked with hydrochloric acid solution from 0.5~6%. In early stage the hydrochloric acid concentrate is usually 4.0% to 6.0%. As the soaking moves, the hydrochloric acid concentrate can be reduced. Collect the hydrochloric acid when the hydrochloric acid concentrate turns to be stable. The demineralized bone, which is named as the ossein and contains >70% collagen peptide content, is the main substrate for gelatin extraction.

In some preferred embodiments, wherein the ossein is grinded to particles that can pass 10 meshes preferably 20 meshes sieves before incubation.

In some preferred embodiments, wherein the incubation of the material comprising collagen with the protease may be performed at a temperature of between 20° C. to 40° C., and/or at a pH of between 4 and 6.

In some preferred embodiments, the process comprises a step of raising the temperature to deactivate the protease after incubation, after the deactivation step an amount of gelatin is extracted and collected.

In some preferred embodiments, after the incubation, increase the temperature to where the protease is deactivated by keeping for, preferably, at least 5 mins, for example, increase the temperature to about 95° C. and keep for about 5~15 min to deactivate the protease.

In some preferred embodiments, the total time for heating and temperature keeping is at least 10 minutes, preferably about 10-20 minutes, for example about 15 minutes, and preferably no more than 30 minutes.

Within the temperature increasing, an amount of gelatin is also released, in some preferred embodiments, after the deactivation step an amount of gelatin is extracted and collected. For example, separate the liquid and solid phase by centrifugation at 10000 rpm for 15 mins, and the ossein in the sediment is collected and go to the next extraction process, and the supernatant is collected, centrifuged again at 10000 rpm for 15 mins and filtrated via 100 meshes gauze. Keep the filtrate and go to following concentration (if needed) and determination process.

In some preferred embodiments, the process comprises a step of a multi-grade extraction, preferably, comprising a step of extraction of the gelatin during a step-by-step heating process, preferably, the temperature of the extraction process is performed at a temperature of between 50° C. and 100° C.

In some preferred embodiments, gelatin can be obtained via a multi-grade extraction by hot water. For example, the hot water temperature can be set in several intervals: (1)50~55° C.; (2) 60~65° C.; (3)70~75° C.; (4)80~85° C.; (5)90~100° C. The gelatin quality and yield may differ from one to another according to different temperatures. The process is usually as below:

(1) Put the ossein from deactivation process in 50~55° C. water, the weight of water is 0.8~1.2 times of the weight of degreased bone. Keep the temperature for 4~8 hs. Separate the liquid and solid phase by centrifugation at 10000 rpm for 15 mins. The ossein in the sediment is collected and go to the next extraction process. The supernatant is collected, centrifuged again at 10000 rpm for 15 mins and filtrated via 100 meshes gauze. Keep the filtrate and go to following concentration (if needed) and determination process.

(2) Put the ossein from step (1) in 60~65° C. water, the weight of water is 0.6~1.0 times of the weight of degreased bone. Keep the temperature for 4~8 hs. Separate the liquid and solid phase by centrifugation at 10000 rpm for 15 mins. The ossein in the sediment is collected and go to the next extraction process. The supernatant is collected, centrifuged again at 10000 rpm for 15 mins and filtrated via 100 meshes gauze. Keep the filtrate and go to following concentration (if needed) and determination process.

(3) Put the ossein from step (2) in 70~75° C. water, the weight of water is 0.5~0.8 times of the weight of degreased bone. Keep the temperature for 3~6 hs. Separate the liquid and solid phase by centrifugation at 10000 rpm for 15 mins. The ossein in the sediment is collected and go to the next extraction process. The supernatant is collected, centrifuged again at 10000 rpm for 15 mins and filtrated via 100 meshes gauze. Keep the filtrate and go to following concentration (if needed) and determination process.

(4) Put the ossein from step (3) in 80~85° C. water, the weight of water is 0.5~0.8 times of the weight of degreased bone. Keep the temperature for 2~6 hs. Separate the liquid and solid phase by centrifugation at 10000 rpm for 15 mins. The ossein in the sediment is collected and go to the next extraction process. The supernatant is collected, centrifuged again at 10000 rpm for 15 mins and filtrated via 100 meshes gauze. Keep the filtrate and go to following concentration (if needed) and determination process.

(5) Put the ossein from step (4) in 90~100° C. water, the weight of water is 0.8~1.2 times of the weight of degreased bone. Keep the temperature for 2~6 hs. Separate the liquid and solid phase by centrifugation at 10000 rpm for 15 mins. Discard the sediment. The supernatant is collected, centrifuged again at 10000 rpm for 15 mins and filtrated via 100 meshes gauze. Keep the filtrate and go to following concentration (if needed) and determination process.

Purification of enzyme extracted gelatin can be varied to achieve the desired level of microconstituents. Filtration can be combined with deionization, oxidation, or a clarification process. The gelatin can be further clarified through flocculation which removes non-gelatin proteins and lipids. Following purification, sequential enzyme produced gelatin extractions may be blended in liquid form prior to concentration. Concentration is achieved through an evaporative process. Concentrated gelatin can be used in liquid form, chilled or dried.

In other aspect, the present disclosure also relates to gelatin obtainable by a process as disclosed herein.

Gelatin is a mixture or peptides and proteins and is extracted from collagen and may also be indicated as collagen hydrolysate of collagen peptide.

The collagen substrate is a helix structure composed of three α-chains, each with a regular Gly-Xaa-Yaa (Xaa is usually Pro, Yaa is usually Hyp or Hyl) sequence repeats. Among the tri-helix areas and the non-helix area in N/C propeptide of collagen molecule, there are some crosslinking formed by mainly by Lys and few His. The interactions, together with the hydrogen bonds, help stable the tri-helix structure.

It was found the protease as disclosed herein can act with certain specificity on the Lysine position, thus can effectively break the crosslinking of Lysine among the chains. Meanwhile, the protease as disclosed herein has also a certain aggressivity to the peptide bonds comprised of other amino acids addition to Lysine. From the substrate structure consideration, the peptide bonds within the non-helix region of N/C propeptides usually have better accessibility to the enzyme, compared with the peptide bonds in the tri-helix region, due to a looser structure. Therefore, the protease as disclosed herein can hydrolyse the N-propeptide and C-propeptide, helping to completely unwind the tri-helix structure prior to degrading the tri-helix chain. In general, the protease's specificity to the peptide bonds comprising of Lysine can provide a high gelatin quality while the certain action on the N/C propeptide can help to get a high yield. Therefore, during the step of incubating the material comprising collagen with the protease as disclosed herein, the yield of high quality gelatin was higher than gelatin obtained with enzymatic processes known in the art.

The present invention is further described by the following examples that should not be construed as limiting the scope of the invention.

Materials and Methods

Protease A, a metalloprotease belonging to family M35, derived from *Thermoascus aurantiacus* and disclosed as amino acids 1-177 of SEQ ID NO: 1 listed herein;

AP 5110, acid protease, commercially available from Doinghiger

Pepsin, commercially available from Sigma

Protease B, Aspergillopepsin II, disclosed as SEQ ID NO: 1 in WO 2014/044626

Protease assays: determination of enzyme protein (EP) content:

The enzyme protein content is determined by Pierce BCA Protein Assay Kits, commercially available from Thermo Scientific. The protein content of three protease used herein is listed as below:

| Enzyme | EP content % (w/w) |
| --- | --- |
| Protease A | 2.7% |
| AP5110 | 7.2% |
| Pepsin | 27.0% |
| Protease B | 2.3% |

Example 1 Gelatin Produced by Protease A, Protease B, AP5110 and Pepsin

Degreased bovine bones were soaked with 4~6% (w/w) hydrochloric acid to remove the minerals, and the hydrochloric acid concentration was reduced gradually as the soaking continued. Stopped the soaking when the hydrochloric acid concentration tended to be stable. Discard the hydrochloric acid solution and get the demineralized bone, which was ossein. The ossein was then natural dried to get about 10% moisture. The dry ossein was then grinded to particles that can pass the 20 meshes sieve.

The dry ossein particles were soaked with of water (water: degreased bone=3:4, w/w) overnight before incubation and pH was adjusted to around 5.0. Either 0.1% Protease A (w/w on the dry ossein, equals to 27 μg EP/g dry ossein) or 0.1% acid protease AP5110 (w/w on the dry ossein, equals to 72 μg EP/g dry ossein) or 0.1% pepsin (w/w on the dry ossein, equals to 270 μg EP/g dry ossein) or 0.117% Protease B (w/w on the dry ossein, equals to 27 μg EP/g dry ossein) was added to the mixture of the ossein and water.

The mixture with protease was incubated at about 28° C. in a water bath for about 2 hours. The solid phase was separated by filtration and washed by water for 3 times, a large part of protease was washed out. New water was added to the washed solid phase with the amount of degreased bone: water=3:5 (w/w), pH of the mixture was adjusted to about 6.0, afterwards the enzyme was deactivated by heating the mixture to about 95° C. within about 7 minutes and maintained for about 8 mins, the total time for heating and temperature keeping is about 15 mins. The ossein particles in the sediment was collected and went to the next extraction process. Kept the supernatant A for collection of gelatin.

The ossein was extracted during a step-by-step heating process as showed in the below table 3. After each extraction process, repeated the above-mentioned separation process and collected the supernatant respectively.

TABLE 3

The conditions of extraction stages

| | Step | | | | | |
| --- | --- | --- | --- | --- | --- | --- |
| | 95° C./ 15 min | 55° C./ 6 h | 65° C./ 5 h | 75° C./ 4 h | 85° C./ 3 h | 95° C./ 5 h |
| S:L (w:w) | 3:5 | 1:1 | 1:0.8 | 1:0.6 | 1:0.6 | 1:1 |
| Temperature ° C. | 95 | 55 | 65 | 75 | 85 | 95 |
| Time (hour) | 0.25 | 6 | 5 | 4 | 3 | 5 |
| Supernatant | A | B | C | D | E | F |

Measured the weight of the supernatant A to F. Measured the refraction of the supernatant using a refractometer, wherein the refraction can reflect the solid content of the supernatant. The total dry matter can be calculated by multiplying the weight and the solid content, consequently the gelatin yield from each stage was calculated respectively, see table 4.

Centrifuge the supernatant A to F at 10000 rpm for 15 mins, discarded the sediment. The new supernatant was then filtrated via a 100 meshes gauze respectively. Kept the filtrate gelatin solution, determine and record the brix value. Calculate the dry matter content and then gelatin yield according to the brix value.

The gelatin solutions were then adjusted to a brix value of 2%, respectively. Then the bloom strength value of the gel solutions was respectively measured with a texture analyzer (TA Plus, commercially available from Stable Micro Systems Ltd) according to the Bloom method from the China national standard GB6783-2013. A commercial gelatin, commercially available from Rousselot and with 240 g bloom value, was also measured as a reference to calculate the bloom of enzymatic gelatin samples. The gelatin bloom from each process was calculated respectively, see table 5.

The below table 4 and table 5 showed the yield and bloom strength of gelatin obtained by the enzymatic extraction processes. According to the results, the protease A indicates a high efficiency with very low enzyme protein dosage. And among the four proteases, Protease A generated the highest yield of high quality gelatin (high quality gelatin means that the strength of the gelatin is above 200 bloom), especially in the early stage extraction stage of comparatively low temperature, and Protease A also achieved the highest total yield and the highest average bloom strength of the total gelatin obtained.

TABLE 4 gelatin yield from each stage

| Enzyme | 95° C./ 15 min | 55° C./ 6 h | 65° C./ 5 h | 75° C./ 4 h | 85° C./ 3 h | 95° C./ 5 h | Total yield |
| --- | --- | --- | --- | --- | --- | --- | --- |
| Pepsin | 3.0% | 0.7% | 0.7% | 1.3% | 3.1% | 6.7% | 15.39% |
| Ap5110 | 2.8% | 0.6% | 0.7% | 1.3% | 3.2% | 6.8% | 15.33% |
| Protease A | 4.2% | 2.2% | 3.0% | 2.8% | 2.6% | 4.6% | 19.32% |
| Protease B | 2.5% | 1.1% | 1.8% | 1.7% | 2.3% | 5.7% | 14.93% |

TABLE 5 gelatin bloom from each stage

| Enzyme | 95° C./ 15 min | 55° C./ 6 h | 65° C./ 5 h | 75° C./ 4 h | 85° C./ 3 h | 95° C./ 5 h | Average bloom |
|---|---|---|---|---|---|---|---|
| Pepsin | 306 | 305 | 292 | 139 | 120 | 73 | 158 |
| Ap5110 | 334 | 246 | 308 | 132 | 97 | 104 | 166 |
| Protease A | 300 | 275 | 224 | 138 | 191 | 63 | 193 |
| Protease B | 219 | 205 | 175 | 136 | 101 | 74 | 130 |

What is claimed is:

1. A method for extracting gelatin, comprising:
   (a) demineralizing a collagen containing material to produce ossein;
   (b) grinding the ossein to particles that can pass 10 meshes sieves;
   (c) incubating the ground ossein in the presence of an effective amount of a protease, and
   (d) extracting the gelatin from the ground ossein, wherein the protease is a metalloprotease belonging to family M35 and comprises of an amino acid sequence having at least 85% identity to amino acids 1-177 of the amino acid sequence SEQ ID NO: 1.

2. The method of claim 1, further comprising, after the incubation and before the extraction, raising the temperature for at least 10 minutes to deactivate the protease.

3. The method of claim 1, further comprising, after the incubation and before the extraction, raising the temperature for at least 5 minutes to deactivate the protease.

4. The method of claim 1, wherein the extraction is a multi-grade extraction, comprising extraction of the gelatin during a step-by-step heating process, wherein the extraction is performed at a temperature of between 50° C. and 100° C.

5. The method of claim 1, further comprising, prior to (a), adding an acid to the collagen containing material for demineralizing.

6. The method of claim 1, wherein the incubation is performed at a temperature of between 20° C. to 40° C., and/or at a pH of between 4 and 6.

7. The method of claim 1, wherein the protease comprises an amino acid sequence having at least 90% identity to amino acids 1-177 of the amino acid sequence SEQ ID NO: 1.

8. The method of claim 1, wherein the protease comprises an amino acid sequence having at least 95% identity to amino acids 1-177 of the amino acid sequence SEQ ID NO: 1.

9. The method of claim 1, wherein the protease comprises an amino acid sequence having at least 99% identity to amino acids 1-177 of the amino acid sequence SEQ ID NO: 1.

* * * * *